United States Patent

Brandt et al.

[11] Patent Number: 6,129,971
[45] Date of Patent: Oct. 10, 2000

[54] TEXTURED, MATTE-FINISH, LOW ADHESION COATINGS

[75] Inventors: Patricia J. A. Brandt, Woodbury; John T. Capecchi, Oakdale; Scott D. Anderson, Lakeland, all of Minn.

[73] Assignee: 3M Innovative Properties Company, St. Paul, Minn.

[21] Appl. No.: 09/039,103

[22] Filed: Mar. 13, 1998

Related U.S. Application Data

[63] Continuation-in-part of application No. 08/852,213, May 6, 1997, abandoned.

[51] Int. Cl.[7] .................................. B05D 5/00; B32B 5/14
[52] U.S. Cl. ........................ 428/141; 428/42.2; 428/42.3; 428/41.8; 428/352; 428/355 N; 428/913; 427/283; 427/257; 427/280; 427/372.2; 427/384
[58] Field of Search .................................. 428/141, 42.2, 428/42.3, 41.8, 352, 355 N, 913; 427/253, 257, 280, 372.2, 384

[56] References Cited

U.S. PATENT DOCUMENTS

| Re. 24,906 | 12/1960 | Ulrich | 206/59 |
|---|---|---|---|
| 2,532,011 | 11/1950 | Dahlquist et al. | 154/53.5 |
| 3,389,827 | 6/1968 | Abere et al. | 220/53 |
| 3,645,835 | 2/1972 | Hodgson | 161/146 |
| 4,112,213 | 9/1978 | Waldman | 526/279 |
| 4,310,509 | 1/1982 | Berglund et al. | 424/28 |
| 4,323,557 | 4/1982 | Rosso et al. | 424/28 |
| 4,327,121 | 4/1982 | Gray, III | 427/44 |
| 4,454,266 | 6/1984 | Coughlan et al. | 524/44 |
| 4,595,001 | 6/1986 | Potter et al. | 128/156 |
| 5,004,630 | 4/1991 | Polski | 427/208.8 |
| 5,026,446 | 6/1991 | Johnston et al. | 156/153 |
| 5,114,739 | 5/1992 | Culbertson et al. | 427/40 |
| 5,214,119 | 5/1993 | Leir et al. | 528/28 |
| 5,290,615 | 3/1994 | Tushaus et al. | 428/40 |
| 5,461,134 | 10/1995 | Leir et al. | 528/14 |
| 5,512,650 | 4/1996 | Leir et al. | 528/14 |
| 5,531,855 | 7/1996 | Heinecke et al. | 156/252 |
| 5,658,661 | 8/1997 | Mitchell, Jr. et al. | 428/352 |

FOREIGN PATENT DOCUMENTS

WO 84/03837  10/1984  WIPO.

OTHER PUBLICATIONS

"GE Silicones—SL6040–D1 Inhibitor", Brochure of General Electric Company, 2 pgs, Mar. 1992.
"GE Silicones—SL6020–D1 Crosslinker", Brochure of General Electric Company, 2 pgs, Mar. 1992.
"GE Silicones—SL6000–D1 Easy Release Polymer, SL 6010–D1 Platinum Catalyst Concentrate", Brochure of General Electric Company, 2 pgs, Mar. 1992.
"13 Gloss", Brochure of BYK—Gardner USA, 2 pgs, undated.
"GE Silicones—SL6000 Solventless Release Coating System", Brochure of General Electric Company, 4 pgs, Oct. 1994.

*Primary Examiner*—William P. Watkins, III
*Attorney, Agent, or Firm*—Stephen W. Bauer; Robert W. Sprague; Ann M. Mueting

[57] ABSTRACT

An article comprising a substrate, and a textured, matte-finish, low adhesion backsize coating on one surface of the substrate, wherein the coating comprises polyvinyl carbamate having nitrogen-bonded hydrocarbon side chains which provide terminal alkyl groups more than five carbons in length.

43 Claims, 4 Drawing Sheets

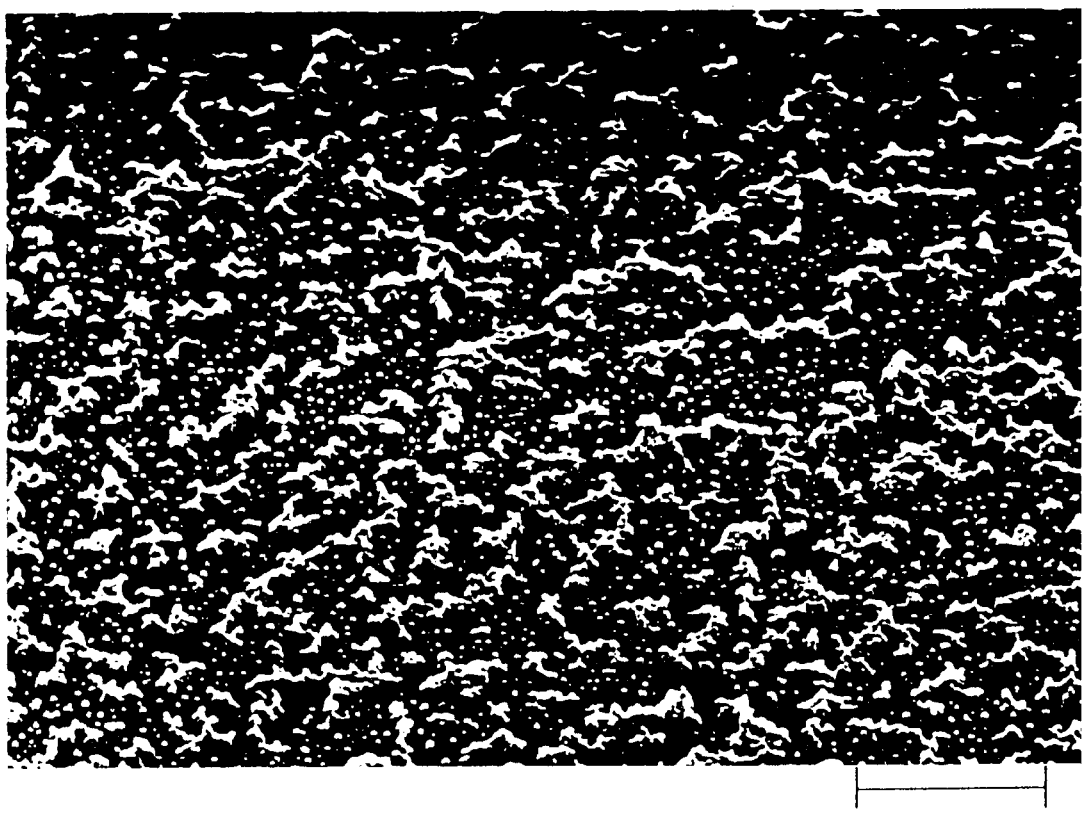
FIG.5  20 μm

FIG.6  20 μm

டி, 129,971

TEXTURED, MATTE-FINISH, LOW ADHESION COATINGS

CROSS-REFERENCE TO RELATED APPLICATION

The present application is a continuation in part of U.S. patent application Ser. No. 08/852,213 filed on May 6, 1997, now abandoned which is incorporated herein by reference.

BACKGROUND OF THE INVENTION

Surface coatings adapted to contact tacky adhesive surfaces with a low degree of adherency thereto are needed so that subsequent separation can be effected with an unusually low removal effort. Such coatings have value, for example, as backsize coatings on pressure sensitive adhesive tapes wound in rolls to permit easier unwinding. They also have value as backsize coatings on pressure sensitive adhesive composite wound dressings delivered by a removable carrier, as well as on target strips on disposable diapers. These coatings, which have a low affinity towards contacting adhesives, are referred to as low adhesion backsize coatings.

A low adhesion backsize coating on the top face of a wound dressing provides the ability to apply and remove tapes and other devices over the dressing, thereby enabling the dressing to be used as a platform for those tapes and other devices. For example, the low adhesion backsize coating allows the tapes and other devices to be removed without also removing or disturbing the underlying dressing and allowing additional contamination to reach the wound. An example of such a dressing is that available under the trade designation "TEGADERM" from 3M Company, St. Paul, Minn.

Typically, wound dressings such as this include polymeric films that are extremely thin, flexible, and supple such that they are conformable. They are typically supplied with a releasable protective liner covering the adhesive coated surface of the film. When the liner is removed and/or when the dressing is rubbed against clothing or bed linens, the adhesive coated film can wrinkle and adhere to itself, interfering with the smooth, aseptic application of the dressing to a patient's skin. Thus, in addition to providing a low adhesion backsize coating on the surface of the film opposite the adhesive, it is also desirable to provide the surface with a low coefficient of friction to reduce edge lift of the dressing when rubbed against bed linens or clothing. Such characteristics are desirable for products other than wound dressings as well.

The coefficient of friction of a surface can be modified by mechanical action on the backing before or after the low adhesion backsize is coated, or by incorporating particulate material into the low adhesion backsize coating. Many articles, however, are too soft to be mechanically roughened. Furthermore, it can be difficult to prepare sufficiently thin coatings with particulate material therein and to keep the particulate material homogeneously suspended and uniformly dispersed during the coating process.

It is also often desirable for a low adhesion backsize to have a matte-finish. This is particularly desirable for wound dressings as a matte-finish surface makes the dressing less visible when applied to the skin. As with the coefficient of friction, the finish of a surface can also be modified by mechanical action on the backing or by incorporating particulate material into the low adhesion backsize coating.

Thus, low adhesion backsize coatings with a low coefficient of friction and a matte-finish are still needed, particularly those that are relatively easy to manufacture.

SUMMARY OF THE INVENTION

The present invention provides an article, such as a wound dressing, comprising a substrate, and a textured, matte-finish, low adhesion backsize coating on one surface of the substrate, wherein the coating comprises polyvinyl carbamate having nitrogen-bonded hydrocarbon side chains which provide terminal alkyl groups more than five carbons in length. The coating is formed from a composition comprising the polyvinyl carbamate and optionally a release modifying material, such as an organopolysiloxane urea, an organopolysiloxane diamine, a silicone resin, a silicone acrylate, or a fluoropolymer. The release modifying material can also be formed in the presence of the polyvinyl carbamate. The gloss of the backsize coating is less than that of the uncoated substrate and less than that of the substrate coated with the same coating composition that is not textured.

The present invention also provides a method of preparing an article comprising a substrate on which is coated a textured, matte-finish, low adhesion backsize coating on one surface of the substrate. The method involves coating a composition comprising polyvinyl carbamate having nitrogen-bonded hydrocarbon side chains which provide terminal alkyl groups more than five carbons in length and a solvent system comprising at least one good solvent for the polyvinyl carbamate and at least one poor solvent for the polyvinyl carbamate in a ratio sufficient to cause precipitation of the polymer upon evaporation of the solvent system.

Also provided is a method of preparing an article comprising a substrate on which is coated a textured, matte-finish, low adhesion backsize coating on one surface of the substrate. The method involves coating a composition comprising a low adhesion backsize polymer and a solvent system comprising a mixture of solvents in a ratio sufficient to cause precipitation of the polymer upon evaporation of the solvent system.

BRIEF DESCRIPTION OF THE DRAWINGS

FIG. 5 is an SEM photomicrograph of a textured, matte-finish, low adhesion backsize coating of the present invention.

FIG. 6 is an SEM photomicrograph of a comparative nontextured low adhesion backsize coating of the same polymer composition as shown in FIG. 5 but delivered from a solvent mixture that contained a low percentage of the poor solvent for the polymer.

DETAILED DESCRIPTION OF PREFERRED EMBODIMENTS

The present invention provides low adhesion backsize coatings with a textured matte-finish surface. Before giving a more detailed discussion of the chemistry of the present textured, matte-finish, low adhesion backsize (LAB) coating compositions, various illustrative products embodying the invention will be described in connection with the accompanying drawings.

Figure 1:
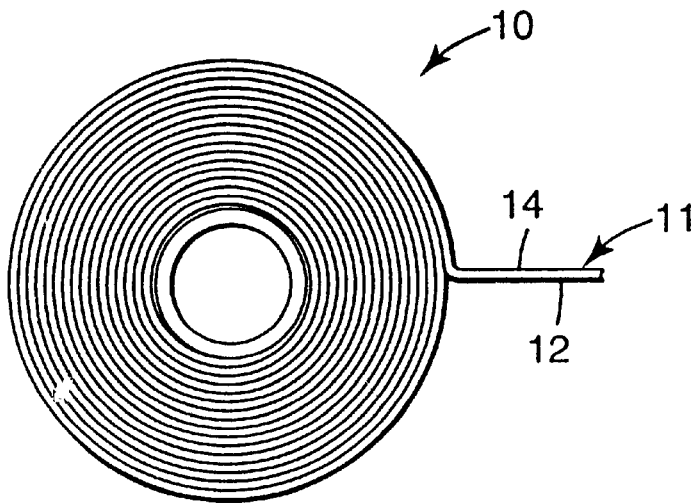
FIG. 1 is a side view of a pressure sensitive adhesive tape including a textured, matte-finish, low adhesion backsize coating of the present invention wound directly upon itself.

FIG. 1 shows a roll 10 of pressure sensitive adhesive tape, such as a surgical tape, wound directly upon itself. The tape includes a backing 11 with a normally tacky pressure sensitive adhesive coating 12 on the face side, and a textured matte-finish low adhesion backsize coating 14 on the back side of the backing 11. The tape is wound so that the adhesive 12 is on the inside. In the roll, the backing 11 serves not only as a permanent base or support for the tacky adhesive coating 12 but also as a temporary liner. This results because the backing 11 in each turn of the roll temporarily contacts and covers the adhesive surface 12 of the overlying turn. The limited adhesion between the backsize coating 14 and the pressure sensitive adhesive 12 makes it possible to unwind the tape with less effort. Moreover, when the tape is unwound, there is less pull of the adhesive upon the back surface of the underlying convolution from which it is separated, thereby reducing the force that tends to cause delamination of the tape structure.

Figure 2:
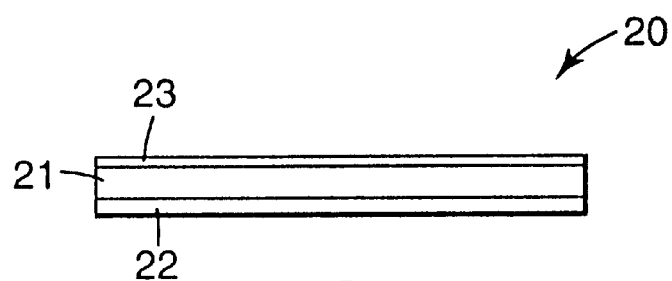
FIG. 2 is a magnified edge view of a pressure sensitive adhesive tape including a textured, matte-finish, low adhesion backsize coating of the present invention.

FIG. 2 shows a magnified edge view of an illustrative tape 20 having a backing 21 coated on the face side with a normally tacky pressure sensitive adhesive 22 and on the back side with a textured, matte-finish, low adhesion backsize coating 23. The backsize coating results in the backing having a back surface which has a lower specific adhesion toward the pressure sensitive adhesive layer than does the inner surface on which the adhesive layer is coated. The resultant differential between the two surfaces aids in reducing or preventing transfer and delamination of the adhesive when the tape is unwound from a roll.

Figure 3:
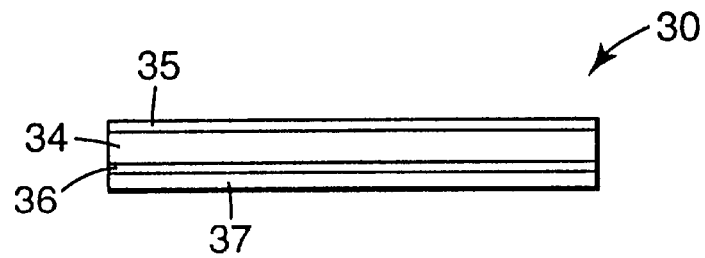
FIG. 3 is a magnified edge view of an alternative embodiment of a pressure sensitive adhesive tape including a textured, matte-finish, low adhesion backsize coating of the present invention.

FIG. 3 shows a magnified edge view of an illustrative tape 30 having a backing 34 provided with a textured, matte-finish, low adhesion backsize coating 35. The face side of the backing 34 is coated with a thin primer layer 36 upon which is coated a pressure sensitive adhesive layer 37. The structure is the same as that of FIG. 2 except for the presence of the primer layer, which serves to bond the adhesive layer to the face side of backing 34 more firmly than would be the case if the primer were omitted. Thus a still further increase in adhesion differential results in respect to the adhesion of the pressure sensitive adhesive to the surface upon which it is coated as compared to its adhesion to the back surface of the tape when wound in a roll. The primer should be of a kind which is highly cohesive, which strongly anchors to the backing film, and which has greater adhesion to the pressure sensitive adhesive than would the surface of the backing film.

An important feature of the present low adhesion backsize is that it has a matte (i.e., dull) finish. On thin film wound dressings, IV dressings, and first-aid dressings, the matte-finish makes the dressing much less visible when applied to the skin due to the lack of reflection of light. Additionally, and significantly, the matte-finish is textured, which provides a much lower coefficient of friction than the same coating that does not have a matte-finish when rubbed against the skin, clothing, or bed linens. In the case of wound and IV dressings, this is beneficial in that it minimizes the potential for edge lift of the dressing when rubbed against skin, bed linens, or clothing. This results in longer wear time for the dressing and therefore less cost. The low adhesion properties provide the capability of removing adhesive products which are placed over the dressing. While a matte-finish surface can be achieved by creating a rough surface by casting or embossing and a low adhesion surface can be achieved by a variety of coatings, the ability to achieve both in one coating operation as occurs in the present invention simplifies, and provides more latitude in, the manufacturing process, which leads to lower cost products.

The release properties of a low adhesion backsize coating can be represented by the peel adhesion of a sample of adhesive-coated tape to the LAB-coated surface. Typically, the peel adhesion (i.e., release) value of a test tape to the backsize coating is less than the peel adhesion value of the test tape to the uncoated substrate (i.e., the substrate) on which the backsize coating is coated.

The textured, matte-finish of the low adhesion backsize coating can be represented by the gloss (i.e., surface reflectance) of the coating. This can be determined by measuring the gloss of the coating at 60° with a gloss meter. The 60° gloss of the textured, matte-finish low adhesion backsize coating of the present invention is less than that of the uncoated substrate and less than that of the substrate coated with the same composition that is not textured. Preferably, the 60° gloss of the textured, matte-finish, low adhesion backsize coating is no greater than about 40, and more preferably, no greater than about 30. Most preferably, the 60° gloss is about 5 to about 15.

The textured, matte-finish of the low adhesion backsize coating can also be represented by the coefficient of friction of the coating, although this can be dependent upon the substrate on which it is coated. The coefficient of friction of the textured, matte-finish, low adhesion backsize coating of the present invention is less than that of the uncoated substrate and less than that of the substrate coated with the same composition that is not textured. Preferably, for polyurethane substrates, the coefficient of friction of a textured, matte-finish, low adhesion backsize coating coated thereon is no greater than about 0.4, more preferably, no greater than about 0.3, and most preferably, about 0.1 to about 0.25.

The textured, matte-finish of the low adhesion backsize coating can also be represented by the surface roughness of the coating. The surface roughness can be reported as the root mean square height averaged over an area ($R_q$), the average height ($R_a$), or the maximum height difference ($R_t$). Regardless of which parameter is used, the surface roughness of the textured, matte-finish, low adhesion backsize coating of the present invention is greater than that of the uncoated substrate and greater than that of the substrate coated with the same composition that is not textured.

Figure 4:
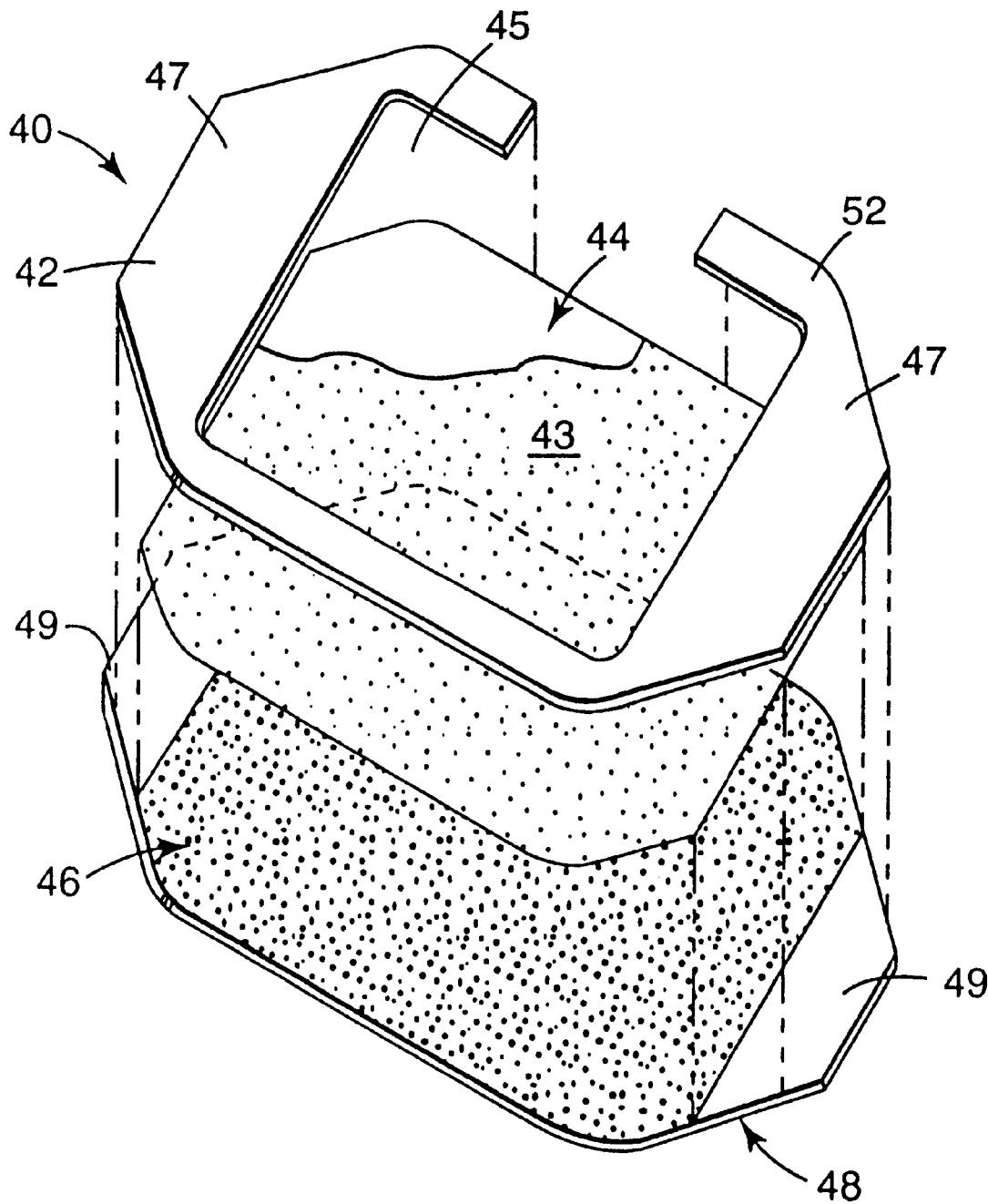
FIG. 4 is a top perspective view of one preferred embodiment of a wound dressing including a textured, matte-finish, low adhesion backsize coating of the present invention.

A low adhesion backsize coating having such properties is particularly desirable for use in a wound dressing. Turning to FIG. 4, one preferred embodiment of an adhesive composite dressing (i.e., wound dressing) 40 comprises a backing 44 which is preferably conformable, a textured, matte-finish, low adhesion backsize coating 43 on a top face of the backing 44; a carrier 52 attached to the top face of the backing 44 over the textured, matte-finish, low adhesion backsize coating 43; a pressure sensitive adhesive 46 on a bottom face of the backing 44; and a liner 48 attached to the exposed surface of pressure sensitive adhesive 46.

In a preferred embodiment, the carrier 52 is attached to backing 44 (over low adhesion backsize coating 43) with a heat seal bond. Thus, the textured, matte-finish, low adhesion backsize coating 43 should be compatible with the heat seal bond between the frame 42 and backing 44. Liner 48 and frame 42 both preferably include tabs 47 and 49 which extend beyond the perimeter of backing 44 to provide a means of applying the backing/frame/adhesive composite without contacting the adhesive 46. The heat seal bond between the carrier 52 and the backing 44 is stronger than the bond between the adhesive 46 and the liner 48. That difference ensures that the backing 44 remains attached to the frame 42 when liner 48 is removed from the adhesive composite dressing 40. In FIG. 4, a rectangular window portion cut in the carrier 42 is removed creating a frame 42 and a window 45 exposing a portion of the top face of the backing 44. Frame 42 provides rigidity to the backing 44 after liner 48 is removed.

In use, liner 48 is first removed from the adhesive composite dressing 40 leaving the frame 42/backing 44/pressure sensitive adhesive 46 intact. The user can then manipulate the adhesive composite dressing 40 using tabs 47 on the frame 42 while viewing the area to which the dressing 40 will be attached through window 45, as the preferred backing 44 is transparent or translucent.

The removal of the window portion of the carrier material 52 which would normally cover window 45 is optional during manufacture. Removal does eliminate one step in the delivery process for previously known window style dressings (i.e., the step of removing a portion of the carrier material from the window 45 prior to removing the liner 48 from the remainder of the dressing 40) and reduces the waste stream at the consumer level. However, some customers prefer that the portion of the carrier 52 normally covering window 45 remains intact until the dressing reaches the end user.

The textured, matte-finish, low adhesion backsize coating 43 on the backing 44 also reduces dressing changes due to unwanted dressing removal when other tapes or devices are placed on the dressing 40 and removed. The textured, matte-finish, low adhesion backsize coating 43 also reduces the surface friction of the dressing 40 on linen or other fabrics, thereby offering additional protection against the accidental removal of dressing 40.

Another article for which the textured, matte-fiinsh, low adhesion backsize coating is useful is a target strip, such as that on a disposable diaper. Such articles are disclosed in U.S. Pat. No. 5,026,446 (Johnston et al.). Briefly, disposable diapers typically have an outer shell of thin plastic film such as polyethylene, which is reinforced at the areas where adhesive closure tabs are adhered during fastening of the diaper around a wearer. The reinforcement frequently is a stronger plastic film that is adhesively attached to the outer shell and is often called a "target strip."

The articles of the present invention are not limited to any particular substrates (i.e., backings) or to any particular pressure sensitive adhesive compositions. The low adhesion backsize composition of the present invention can be applied by coating from solution upon a wide variety of substrates (typically in the form of a film) to which the ultimate dried backsize coating will be firmly bonded so as to prevent delamination under the pull of the contacting adhesive when the tape is unwound from rolls.

Examples of substrates (e.g., backing films) suitable for use in the present invention can be made from cellophane, plasticized cellulose acetate, ethyl cellulose, benzyl cellulose, cellulose butyrate, cellulose aceto-butyrate, cellulose nitrate, etc. A suitable glassine paper can also be used. Examples of noncellulosic substrates are the various vinyl polymer films such as those made from polyvinyl acetate, copolymers of vinyl acetate and vinyl chloride, polyvinyl butyral, and polyvinylidene chloride, as well as polyolefins such as polyethylene and polypropylene, polyurethanes, etc. Various other backing films are known to those skilled in the art.

Examples of polymers that are suitable for use as wound dressing films in the present invention include polyurethane such as that available under the trade designation "ESTANE" (B F Goodrich, Cleveland, Ohio), elastomeric polyester such as that available under the trade designation "HYTREL" (DuPont, Wilmington, Del.), polyethylene, blends of polyurethane and polyester, chlorinated polyethylene, styrene/butadiene block copolymers such as that available under the trade designation "KRATON" (Shell Chemical Company, Houston, Tex.), polyether block amides such as that available under the trade designation "PEBAX" (distributed by Rilsan Corp., Glen Rock, N.J.), and polyvinyl chloride. Particularly preferred substrates are elastomeric polyurethane, polyester films or polyether block amides. These films combine the desirable properties of resiliency, high moisture vapor permeability, and transparency. U.S. Pat. Nos. 3,645,835 (Hedgson) and 4,595,001 (Potter et al.) describe methods of making high vapor/moisture permeable films and methods for testing their permeability.

The pressure sensitive adhesive can be one of numerous materials. Examples of useful pressure sensitive adhesives include inherently tacky materials, such as some poly(meth) acrylates or selected polyolefins, and elastomeric materials that are combined with tackifying resins to attain required levels tackiness and cohesive strength. Tackified natural rubber and block copolymers are examples of this latter class of pressure sensitive adhesive materials.

For medical applications, the adhesives are those that are safe to use on human skin. Preferred such adhesives are those that are of the class known as "hypoallergenic." Certain acrylate copolymers are adhesives of this class. Suitable pressure sensitive adhesives that can be used in medical applications include, for example, the acrylate copolymers described in U.S. Pat. No. Re. 24,906 (Ulrich), particularly a 97:3 isooctyl acrylate:acrylamide copolymer. Other usefil adhesives are those described in U.S. Pat. No. 3,389,827 (Abere et al.), which discloses block copolymers having three or more polymer block structures having a general configuration -A-B-A- wherein each A block is a thermoplastic polymer with a glass transition temperature above room temperature (i.e., above about 20° C.) having an average molecular weight of about 5,000 to about 125,000 and the B block is a polymer of a conjugated diene having an average molecular weight of about 15,000 to about 250,000. Additional examples of useful adhesives are isooctyl acrylate/n-vinyl pyrrolidone copolymer adhesives and crosslinked acrylate adhesives such as, for example, those described in U.S. Pat. No. 4,112,213 (Weldman). Pressure sensitive adhesive compositions that include a blend of discrete, crosslinked polymer microspheres and a polymer matrix suitable for skin contact are described in detail in U.S. patent application Ser. No. 08/726,513, filed Oct. 7, 1996 pending. Inclusion of medicaments or antimicrobial agents such as iodine in the adhesive is useful for reducing skin flora and preventing infection. U.S. Pat. Nos. 4,310,509 (Berglund et al.) and 4,323,557 (Rosso) describe such antimicrobial adhesives.

A further description will now be given of the chemistry of the textured, matte-finish, low adhesion coating compositions. These compositions include a polyvinyl carbamate having nitrogen-bonded hydrocarbon side chains which provide terminal alkyl groups more than five carbon atoms in length. Such polymers may be made by reacting polyvinyl alcohol with an appropriate monofunctional isocyanate. Examples of such polymers are described in U.S. Pat. No. 2,532,011 (Dahlquist et al.). In the Dahlquist et al., these polymers are described for use as low adhesion backsize coatings, however, they are not described as having a substantially uniform textured, matte-finish surface; rather, they were coated to form a smooth, glossy film (see column 10, lines 22–23 of Dahlquist et al.). Thus, although the compositions may be the same, the resultant coatings are different.

Polyvinyl alcohol is customarily made by hydrolyzing polyvinyl acetate so as to replace acetate groups with hydroxyl groups. The polyvinyl alcohols of commerce retain some acetate groups, as the hydrolysis and replacement is not entirely complete. Reaction with the isocyanate results in replacement of hydroxyl groups by carbamate groups, which form long side chains attached to carbon atoms of the extremely long linear vinyl chain, these side chains providing nitrogen-linked chains terminating with alkyl groups. For present purposes, the polyvinyl alcohol need not be a highly hydrolyzed polyvinyl acetate. For example, polyvinyl carbamate polymers can be made from both 88 mole percent and 50 mole percent hydrolyzed polyvinyl acetates, with substantially the same effectiveness. In the latter case the carbamate side chains are at most attached to only one-fourth of the carbon atoms in the linear vinyl chain. Hydrophobic low adhesion polymers can be obtained even when as few as five percent of the carbon atoms of the vinyl chain have attached carbamate side chains, although for a textured, matte-finish coating there are preferably about 50 mole percent to about 88 mole percent carbamate side chains.

The polyvinyl carbamates are not limited to those containing only acetate groups and hydroxyl groups at the existing possible points of attachment not occupied by carbamate groups. The polyvinyl acetate may be a copolymer. Thus a hydrolyzed ethylene:vinyl acetate copolymer can be reacted with octadecyl isocyanate to obtain a polyvinyl carbamate, which has the advantage of a higher softening point than that obtained with use of straight hydrolyzed polyvinyl acetate. Polyvinyl carbamate molecules containing residual hydroxyl groups can be chemically cross linked to increase heat resistance, as by reacting with a small proportion of an appropriate diisocyanate.

The simple alkyl isocyanates have the general formula $(C_\eta H_{2\eta+1}).N=C=O$ where $\eta$ should have a value of more than five (preferably at least 14 and more preferably at least 18) for making the desired polyvinyl carbamate coating compositions. These monofunctional isocyanates are to be distinguished from the polyfunctional diisocyanates. Octadecyl isocyanate has the formula $C_{18}H_{37}.N=C=O$ and hence has 18 carbon atoms in the nitrogen-linked alkyl chain. When this is reacted with polyvinyl alcohol (hydrolyzed polyvinyl acetate), the resulting N-octadecyl carbamate side chains have the structure indicated by the $C_{18}H_{37}.N(H)C(O)O—C—H$ where the carbon atom at the extreme right is one of those in the lengthy vinyl skeleton chain. The nitrogen-linked group need not be a continuous aliphatic hydrocarbon chain, and may include other atoms or radicals capable of being present in the isocyanates, provided that they do not interfere with the desired low adhesion property of the polyvinyl carbamate.

The textured, matte-finish, low adhesion coating should be normally solid and should retain a stable low adhesion characteristic at temperatures above room temperature (e.g., 25–30° C.). The greater the side chain length the easier it is to purify the polyvinyl carbamate so as to remove substances of low molecular weight present in the reaction product, and which decrease the effectiveness as low adhesion coatings.

The textured, matte-finish, low adhesion backsize coatings of the present invention can be of various thicknesses. Preferably, the textured, matte-finish, low adhesion backsize coating is of a thickness such that it does not crack, rupture or flake when the article is bent at a sharp angle or creased. Such coatings can be extremely thin. For example, it has been found that one pound of polyvinyl N-octadecyl carbamate suffices for coating 5000 square yards of cellophane tape backing. Such a coating is less than one-hundred-thousandth of an inch thick and constitutes a "molecular film" (i.e., a film which has a thickness of only a relatively few molecules). In commercial practice it sometimes may be found more convenient to apply a coating which is considerably thicker than the possible minimum.

A feature of the present backsize coating is that it is hydrophobic (water-repellent) and provides a waterproof back surface. This is of particular value when the backing film is permeable to water and quickly becomes soft and weak when in contact with water. The backsize coating does not greatly change the moisture-vapor permeability of the backing, as it is not moisture-proof with respect to water vapor.

The textured, matte-finish, low adhesion backsize coating can be applied from a dilute solution of a volatile organic solvent system using any typical coating procedure followed by drying to remove the solvent system. Applicants have discovered that the polyvinyl carbamates described above, which are known to produce low adhesion backsize coatings, can also produce textured, matte-finish, low adhesion backsize coatings. Such advance has resulted from the discovery that the solvent system out of which the polyvinyl carbamate is coated can effect its texture and surface finish.

The solvent system is one that dissolves the polymer of the low adhesion backsize coating composition, but upon evaporation, the polymer precipitates out of solution such that there is phase separation. The solvent system includes a mixture of good and poor solvents for the polymer. A "good solvent" is one that dissolves the polymer over a broad concentration range and from which the polymer does not precipitate upon dry down (i.e., upon evaporation of the solvent). In contrast, a "poor solvent" is one that may dissolve the polymer, although it would be over a limited concentration range, from which the polymer precipitates upon dry down. That is, as the solvent system evaporates, the composition becomes enriched in a poor solvent for the polymer and the polymer phase separates (i.e., precipitates) to form a textured matte-finish surface, rather than remaining homogeneous and forming a smooth film. Thus, the solvent system provides a controlled precipitation of the polymer during dry down (rather than before coating), thereby forming a substantially uniform textured surface, rather than the smooth glossy film of U.S. Pat. No. 2,532,011 (Dahlquist et al.). The composition may need to be heated slightly to ensure that the polymer remains in solution until after it is coated out. If coated from the appropriate combination of good and poor solvents, the textured coating of the present invention is sufficiently stable and adherent such that cracks do not form either during or after coating, thereby forming a substantially uniformly distributed coating.

The solvent system includes at least one good solvent for the polymer and at least one poor solvent for the polymer. Preferably, the good solvent is an aromatic solvent such as toluene or xylene, an alkane such as heptane, ethyl acetate, or mixtures thereof. Preferably, the poor solvent is an alcohol. More preferably, the good solvent is an aromatic solvent, such as toluene or xylene, optionally in combination with an alkane, and the poor solvent is a lower alcohol (i.e., a $C_1–C_4$ alcohol). Although methanol as the poor solvent has not been effective at producing the desired textured coating, it is believed that it could be effective with the appropriate good solvent and in the appropriate amount. Most preferably, the good solvent is xylene, toluene, or a mixture thereof, optionally in combination with heptane, and the poor solvent is ethanol, 2-propanol, or a mixture thereof. The ratio of the good solvent to the poor solvent can be determined by one skilled in the art without undue experimentation. Typically, the poor solvent is used in at least about 50 weight percent, based on the total weight of the solvent system, although this can vary depending on the particular solvents used.

The textured, matte-finish, low adhesion backsize coatings of the present invention need not consist exclusively of the indicated polyvinyl carbamates. The latter may be blended with other release materials (referred to herein as a "release modifying material") and/or with a material that enhances the durability of the coating. Such additional materials are selected such that they are sufficiently soluble in the solvent system described above to achieve the textured, matte-finish. Release modifying materials may be durability enhancing and vice versa. Typically, however, they are distinct materials. For example, other release modifying materials include low release polymers, such as organopolysiloxane ureas, organopolysiloxane diamines, silicone resins, silicone acrylates, fluoropolymers, and the like. Examples of organopolysiloxane release materials are disclosed, for example, in U.S. Pat. Nos. 5,214,119 (Leir et al.), 5,461,134 (Leir et al.), and 5,512,650 (Leir et al.). Such blends can also be prepared by forming the release modifying material in the presence of the polyvinyl carbamate. For example, a polyorganosiloxane urea-modified polyvinyl carbamate low adhesion backsize coating can be prepared by first blending the polyvinyl carbamate with reactive mixture of an organopolysiloxane diamine, a diisocyanate and optional chain extender. The polyorganosiloxane urea release modifying material can then be formed in situ by exposing this blend to conditions required to polymerize the reactive mixture. Release modifying materials can be used in amounts up to about 70 weight percent, based on the total weight of solids of the composition, without adversely affecting the textured matte-finish characteristics.

In certain situations, such as with first aid dressings that are exposed to highly abrasive conditions, a textured, matte-finish, low adhesion coating of the present invention can include a polymer that enhances the durability of the coating. Thus, preferably, the textured, matte-finish, low adhesion coating compositions of the present invention include a polymer that enhances coating durability blended with a polyvinyl carbamate and optionally a release modifying material. Durability can be determined by subjecting the coating to abrasive conditions and determining the gloss of the coating, as described above. Preferably, for a durable coating, the gloss reading does not increase significantly before and after subjecting it to abrading conditions. Preferably, for a durable coating, the 60° gloss reading does not increase by more than about 20 gloss units after 200 cycles of the abrasion described in Example 13.

Such durability enhancing polymers are those that have a relatively high glass transition temperature (Tg). Preferably, they have a Tg of at least about 40° C. Examples of such durability enhancing polymers include polyvinyl butyral and polyethyloxazoline. Polyvinyl butyral is a particularly preferred material. Durability enhancing polymers can be used in amounts of at least about 5 weight percent and up to about 75 weight percent, based on the total weight of solids of the composition, without adversely affecting the textured matte-finish characteristics.

Advantages of the invention are illustrated by the following examples. However, the particular materials and amounts thereof recited in these examples, as well as other conditions and details, are to be interpreted to apply broadly in the art and should not be construed to unduly limit the invention.

METHODS

Coefficient of Friction

The coefficients of friction of the cured low adhesion backsize (LAB) coatings were determined by the following procedure, based on ASTM D1894-63, sub-procedure A. An approximately 25 centimeter (cm)×15 cm area of the LAB-coated substrate was adhered to the platform of an IMASS Slip/Peel tester (model SP-102B-3M90 available from IMASS Inc., Accord, Mass.) such that the LAB-coated surface was exposed. Care was taken to insure that the LAB surface of the LAB-coated substrate was untouched, uncontaminated, flat, and free of wrinkles. The sample surface and the friction sled (model SP-101038 available from IMASS Inc., Accord, Mass.) wrapped with 3.2 millimeter (mm) thick, medium-density foam rubber) were blown with compressed air to remove any loose dust or debris, the friction sled was placed on the LAB surface, and the chain attached to the sled was affixed to the force transducer of the IMASS Slip/Peel tester. The platform of the IMASS Slip/Peel tester was set in motion at a speed of 15 cm/minute, thereby dragging the friction sled across the LAB surface. The instrument calculated and reported the average kinetic frictional force, omitting the static frictional force. The kinetic coefficient of friction was obtained by dividing the kinetic frictional force by the weight of the friction sled.

Gloss

Gloss (i.e., surface reflectance) was measured by placing the LAB-coated laminate on an opaque surface and reading the gloss using a BYK-Gardner Micro Tri-Gloss meter (BYK Gardner, Silver Spring, Md.) set to read at 60 degrees (60°).

Surface Roughness

Surface roughness was measured using an RST Plus Surface Profiling System (WYKO Corporation, Tucson, Ariz.) set up in the vertical-scanning interferometry mode using a 50× Mirau interference objective with a Numerical Aperture (N.A.) of 0.55. Samples were prepared by cutting 20 mm×50 mm strips of sample. These samples were tacked to cleaned glass slides using 3M "MAGIC MENDING TAPE" (3M Company, St. Paul, Minn.). The samples were prepared for examination by applying a Au/Pd coating to minimize interference effects which may occur when the light is reflected off of the top surface of the coating and off the coating substrate interface. Samples were placed in a Denton DeskII Cold Sputter/Etch unit. Three coating passes were used to sputter a sufficiently thick (approximately 40 nm) coating of Au/Pd. Each sputter coating pass was at 20 Ma and lasted for 20 seconds. The sample was allowed to cool for 3 minutes before the next pass was started. An area of 45 micrometers×60 micrometers was analyzed for each sample. The image size was 368 pixels by 238 pixels with a pixel aspect ratio of 1.16. Curling and buckling of the samples created some long range variations in surface height that influenced the calculations of the surface roughness parameter. To overcome this problem an 80/mm digital high pass filter was imposed on the data.

The data reported in the table below is the root mean square height averaged over the area $$\left(R_q = \frac{1}{n}\left[\sum_{i=1}^{n} z_i^2\right]^{1/2}\right),$$

the average height $$\left(R_a = \frac{1}{n}\sum_{i=1}^{n} |z_i|\right) \text{ and}$$

and the maximum height difference ($R_t = z_{max} - z_{min}$). (Where z at a point is the calculated mean elevation at a point minus the measured elevation at that point; the calculated mean elevation at the point is the elevation of the best fit plane at the point when the tilt correction is applied.)

Peel Adhesion of Adhesive Tape to LAB-Coated Laminates

To measure adhesion of adhesive tape to the LAB-coated laminates of Examples 1, 2, 4, and 7, 1.25×7.6 cm strips of "TRANSPORE" tape (3M Company, St. Paul, Minn.) were placed on the LAB-coated substrate and pressed in place by passing a 4 pound roller over the tape sample two times. The force required to remove the tape was determined using an Instron (Canton, Mass.) model 1122 material testing instrument. The adhesive laminate with the "TRANSPORE" tape sample was first adhered to a frictionless aluminum wheel which is wrapped with double stick adhesive tape (3M Company, St. Paul, Minn., Cat. No. 443-PC) and 3M "SCOTCH" Brand 851 tape (adhesive side out). This was fitted into the lower jaw of the Instron material testing instrument. One end of the tape was then gripped by a clamp which was attached to a 2000-gram load cell mounted in the upper part of the instrument. The tape was peeled from the laminate at a rate of 12 inches/minute (30.5 cm/minute). Recordings were made of both the force required to remove the tape from the laminate and the time interval from when the tape was first applied until the tape was removed from the laminate.

Peel Adhesion of LAB Coated on Biaxially Oriented Polypropylene (BOPP)

The LAB solution of Example 3 was coated on six inch (15.2 cm) wide freshly corona treated 1.0 mil (25.4 micrometers) thick BOPP using a 200 pyramidal gravure roll and dried. The peel adhesion testing was carried out at constant temperature (approximately 21° C.) and humidity (50% relative humidity) using a constant rate Instron tensile tester with a 135° test jig secured in the lower jaw. A 5 cm×12.5 cm piece of the sample to be tested was securely adhered to a steel panel using a piece of double-coated adhesive tape (available from 3M Company under the trademark "STA-305"). The 2.54 cm wide pressure-sensitive adhesive test tape described below with a leader attached was then centered over the test sample and was immediately rolled down lengthwise (two passes) with a 4.5 pound (2.0 kilogram) hard rubber roller. The panel was then placed into the jig in the lower jaw of the tensile tester and the adhesive tape was placed into the upper jaw. The upper jaw was set in motion at a constant crosshead speed of 12 inches/minute (30.5 cm/minute) while the steel panel was moved so as to keep the adhesive test tape at a 135° angle to the panel. The force required to remove the adhesive test tape from the sample was recorded as the 135° peel adhesion. Results are reported in grams/inch and Newtons/centimeter (N/cm) and are an average of at least two independent measurements.

The test tape used a cast polypropylene film backing (PP resin was No.3576 from Fina, Dallas, Tex.) with a basis weight of approximately 5 mils (127 micrometers). The adhesive composition was: 45 parts "WINGTACK" Plus solid C5 tackifying resin, available from Goodyear Chemical, Akron, Ohio; 40 parts "KRATON" 1111 styrene-isoprene-styrene linear block copolymer having a styrene content of about 21 percent, approximately 15 percent diblock, and 85 percent triblock, available from Shell Chemical, Houston, Tex.; 14 parts "SHELLFLEX" 371 naphthenic oil, available from Shell Chemical; 1 part "IRGANOX" 1076 antioxidant, available from Ciba Geigy, Hawthorne, N.Y. The adhesive coating thickness was approximately 10–12 grains/24 inch$^2$ (38–51 micrometers).

Method of Preparing Polyvinyl Carbamates

Polyvinyl carbamates were prepared following the general teachings of U.S. Pat. No. 2,532,011 (Dahlquist et al.) with modifications described below. The polyvinyl alcohol (available from a number of sources such as Air Products, Allentown, Pa., DuPont, Wilmington, Del., or Wacker, Munich, Germany) was suspended in xylene in a reaction vessel equipped with a reflux condenser and water trap. A volume of xylene necessary to produce a final product solution at 40 percent solids was used. Moisture in the polyvinyl alcohol was removed by heating the system at reflux. Based on the hydroxyl content of the polyvinyl alcohol, a stoichiometric amount of octadecyl isocyanate (Bayer, Leverkusen, Germany) was added. Heating at reflux was continued until the isocyanate was consumed as determined by FTIR (disappearance of band at 2230 cm$^{-1}$). Disappearance of the polyvinyl alcohol, which is insoluble in xylene prior to reaction with the octadecyl isocyanate, was visually monitored. The soluble reaction product was cooled, diluted to the desired solids level with the desired solvent(s), and filtered.

Preparation of Adhesive "ESTANE" 58309 Laminate

Twenty-five grams per square meter of a pressure sensitive adhesive prepared in accordance with U.S. Pat. No. Re. 24,906 (Ulrich), comprising a copolymer of 96 percent isooctyl acrylate and 4 percent acrylamide, was applied to a silicone-coated kraft paper release liner (2-60BKG-157-99AM, Daubert Coated Products, Inc., Willowbrook, Ill.) using a standard horizontal knife coater.

A 25 micrometer thick film of "ESTANE" 58309NAT022 polyurethane resin (B. F. Goodrich, Cleveland, Ohio) was extruded and laminated to the adhesive surface to form the backing for the dressings. This laminate is referred to as "ESTANE" 58309 polyurethane/adhesive laminate.

Preparation of Adhesive "ESTANE" 58237 Laminate

An adhesive composition featuring a pressure sensitive adhesive matrix blended with polymeric microspheres was prepared as follows. To prepare the microspheres, a monomer mixture was prepared by dissolving 4.8 grams of acrylic acid, 2.4 grams of "CARBOWAX" 750 acrylate (polyethylene oxide acrylate), and 1.13 grams "LUCIDOL" 70 (70 percent benzoyl peroxide) in 232.8 grams of isooctyl acrylate. A surfactant solution was prepared by dissolving 0.75 gram of sodium dodecyl benzene sulfonate in 360 grams of water. The monomer mixture was then added to the surfactant solution, and the resulting mixture was emulsified using a "GIFFORD-WOOD" mixer until the droplet size was less than 5 micrometers. The emulsion was charged to a 1 liter baffled reactor, heated to 65° C., degassed with $N_2$, and allowed to react for 8 hours. Microspheres having an average diameter of about 2 micrometers were formed during the reaction period.

The adhesive matrix was prepared according to the procedures described generally in International Publication No. WO 84/03837 (3M Company) using a monomer mixture containing 70 parts by weight isooctyl acrylate, 15 parts by weight acrylic acid, and 15 parts by weight "CARBOWAX" 750 acrylate (polyethylene oxide acrylate). The matrix was then blended with the microspheres (27 parts microspheres per hundred parts matrix) using a Lightening-brand mixer and applied to a silicone-coated kraft paper release liner (2-60BKG-157-99AM, Daubert Coated Products, Inc., Willowbrook, Ill.) coated on the higher bonding side.

Next, a 25 micrometer thick film of "ESTANE" 58237 thermoplastic polyurethane (B. F. Goodrich Co.) was extruded and laminated to the adhesive composition. The thickness of the adhesive composition was 25 micrometers. This laminate is referred to as "ESTANE" 58237 polyurethane/adhesive laminate.

EXAMPLES

Example 1

Blend of Polyoctadecyl Carbamate-co-Vinyl Acetate with Polydiorganosiloxane Urea on a Polyurethane Substrate Polydiorganosiloxane urea was first made by adding 3.10 grams of isophorone diisocyanate (IPDI, available from Huls, Theodore, Ala., or Bayer, Baytown, Tex.) to a solution of 1.13 grams of a 5000 Mn polydimethylsiloxane diamine (PDMS, prepared following Example 38 of U.S. Pat. No. 5,512,650 (Leir et al.), except that the disiloxane:cyclic monomer ratio was adjusted to produce a 5000 Mn PDMS) and 1.40 grams of 1,3-diaminopentane (available under the trade designation "DYTEK" EP from DuPont) in 219.38 grams of 2-propanol at 25° C., with a slow nitrogen purge, and stirring for 15 minutes. The resulting polydiorganosiloxane urea consisted of 20 weight percent polydimethylsiloxane and 80 weight percent "DYTEK" EP/IPDI at 2.5 percent solids in 2-propanol. The solution was further diluted to 1.3 percent solids by the addition of 211.05 grams of 2-propanol. To 100 grams of this solution was added with agitation, a solution of 2.57 grams of a polymer component, polyoctadecyl carbamate-co-vinyl acetate having 50 mole percent octadecyl carbamate (prepared in xylene at 40 percent solids as described above), in 50.38 grams of a solvent blend of heptane/xylene/2-propanol (72/25/3 weight ratio). The final product mixture was a homogenous, hazy 2.5 percent solids solution of a polymer component (polyoctadecyl carbamate-co-vinyl acetate) and a polydiorganosiloxane urea-containing component in a 2:1 weight ratio. The solution was coated onto an "ESTANE" 58309 polyurethane/adhesive laminate prepared as described above using a No. 3 wire wound rod (RD Specialties, Webster, N.Y.) and allowed to air dry. A matte-finish was observed on the coated film. Gloss was measured. The 60° gloss reading of the uncoated and coated films were 78.5±1.3 and 13.2±2.6, respectively (gloss units). Peel adhesion was measured by adhering samples of "TRANSPORE" tape (3M Company, St. Paul, Minn.) to the coated film as described above. After 24 hours the tape was removed using an Instron Model 1122 material testing instrument equipped as described above. The coated film gave a release value of 83.2±10.6 grams/inch (0.321±0.041 N/cm) compared to the control (uncoated film) value of 166.4±36.9 grams/inch (0.642±0.014 N/cm).

Example 2

Preparation of a Blend of Polyoctadecyl Carbamate-co-Vinyl Acetate with In Situ Polymerized Polydiorganosiloxane Urea on a Polyurethane Substrate To a solution of 46.70 grams of polyoctadecyl carbamate-co-vinyl acetate having 50 mole percent octadecyl carbamate (prepared in xylene at 40 percent solids as described above) in a solvent mixture of 27.48 grams of 2-propanol, 229.03 grams of xylene, and 659.60 grams of heptane, was added 1815.08 grams of 2-propanol, 4.67 grams of 5000 Mn polydimethylsiloxane diamine (PDMS, prepared following Example 38 of U.S. Pat. No. 5,512,650 (Leir et al.), except that the disiloxane:cyclic monomer ratio was adjusted to produce a 5000 Mn PDMS), and 5.82 grams of 1,3-diaminopentane (available under the trade designation "DYTEK" EP from DuPont) with stirring at 25° C. Next, 12.85 grams of isophorone diisocyanate (IPDI, available from Huls or Bayer) was added at 25° C. with stirring and a slow nitrogen purge. The mixture was stirred for 30 minutes, and in the presence of the polyoctadecyl carbamate-co-vinyl acetate, the IPDI reacted with the PDMS diamine and the "DYTEK" EP to form a polydiorganosiloxane urea-containing component with 20 weight percent PDMS and 80 weight percent "DYTEK" EP/IPDI. The final product mixture was a homogenous, hazy 2.5 percent solids solution of a polymer component (polyoctadecyl carbamate-co-vinyl acetate) and a polydiorganosiloxane urea-containing component in a 2:1 weight ratio. The solution was coated onto an "ESTANE" 58309 polyurethane/adhesive laminate prepared as described above using a No. 16 wire wound rod (RD Specialties, Webster, N.Y.) and allowed to air dry. A matte-finish was observed on the coated film. Gloss was measured. The 60° gloss reading of the uncoated and coated films were 82.8±1.1 and 5.5±0.2, respectively. To measure peel adhesion, samples of the film were laminated to samples of "TRANSPORE" tape (3M Company, St. Paul, Minn.), and after 16 hours the tape was removed using an Instron Model 1122 material testing instrument equipped as described above. The coated film gave a release value of 32.9±1.9 grams/inch (0.127±0.007 N/cm) compared to the control (uncoated film) value of 131.2±9 grams/inch (0.507±0.035 N/cm).

Example 3

Preparation of a Blend of Polyoctadecyl Carbamate-co-Vinyl Acetate with In Situ Polymerized Polydiorganosiloxane Urea on Biaxial Oriented Polypropylene (BOPP)

To a solution of 1.13 grams of a 5000 Mn polydimethylsiloxane diamine (PDMS, prepared following Example 38 of U.S. Pat. No. 5,512,650 (Leir et al.), except that the disiloxane:cyclic monomer ratio was adjusted to produce a 5000 Mn PDMS) and 1.42 grams of 1,3-diaminopentane (available under the trade designation "DYTEK" EP from DuPont) in 219.38 grams of 2-propanol at 25° C. was added a solution of 10.63 grams of polyoctadecyl carbamate-co-vinyl acetate having 50 mole percent octadecyl carbamate (prepared in xylene at 40 percent solids as described above) in 145.36 grams of heptane, 50.47 grams of xylene, and 218.54 grams of 2-propanol. With stirring and a slow nitrogen purge, 3.08 grams of isophorone diisocyanate (IPDI, available from Huls or Bayer) was slowly added to the mixture. In the presence of the polyoctadecyl carbamate-co-vinyl acetate, the IPDI reacted with the PDMS diamine and the "DYTEK" EP to form a polydiorganosiloxane urea-containing component with 20 weight percent PDMS and 80 weight percent "DYTEK" EP-IPDI. The final product mixture was a homogenous, hazy 2.6 percent solids solution of a polymer component (polyoctadecyl carbamate-co-vinyl acetate) and a polydiorganosiloxane urea-containing component in a 1.9:1 weight ratio. The solution was coated on 15 cm wide freshly corona treated 25 micrometer thick biaxially oriented polypropylene (BOPP) using a 200 pyramidal gravure roll and dried. A matte appearance was observed for the coated BOPP film. Gloss was measured. The 60° gloss reading was 11 for the coated BOPP and 145 for the uncoated BOPP control. Peel adhesion was measured following the test described above. An average peel value of 340 grams/inch (1.313 N/cm) was obtained when the test tape was peeled at 12 inches/minute (30.5 cm/minute) from the coated BOPP at a 135° angle using an Instron tensile tester.

Example 4

Effect of Polyvinylcarbamate: Polydiorganosiloxane Urea Ratio on Matte and Release Properties The polydiorganosiloxane urea-containing component described in Example 1 was blended with polyvinyloctadecyl carbamate-co-vinyl acetate having 50 mole percent octadecyl carbamate described in Example 1 to create blend ratios (wt/wt) varying from 1:1 to pure polyvinyloctadecyl carbamate-co-vinyl acetate. These were coated onto an "ESTANE" 58309 polyurethane/adhesive laminate prepared as described above using a 90 lines/inch (35 lines/cm) ruling mill gravure roll and dried at 70° C. The film samples were tested for gloss and peel adhesion to "TRANSPORE" tape (3M Company, St. Paul, Minn.) 24 hours after application as described in Example 1. The results are shown in the table below.

| LAB Composition (Polyvinylcarbamate: Polysiloxane Urea) | 60° Gloss Meter Reading | Peel Adhesion, grams/inch (N/cm) |
| --- | --- | --- |
| 1:1 | 13.2 | 56.0 (0.216) |
| 2:1 | 10.3 | 78.3 (0.302) |
| 3:1 | 7.6 | 93.3 (0.360) |
| 4:1 | 7.1 | 105 (0.405) |
| 1:0 | 11.0 | 108.3 (0.418) |
| Uncoated film | 72.6 | 298 (1.151) |

These results indicate a matte-finish can be achieved in the presence of added polymeric components and these additives can be used to control adhesion and release properties.

Example 5

Effect of Solvent Ratio on Matte-finish

Polyvinyloctadecyl carbamate-co-vinyl acetate was dissolved in various solvent mixtures and coated onto an "ESTANE" 58309 polyurethane/adhesive laminate prepared as described above using a No. 14 wire wound rod (RD Specialties, Webster, N.Y.) and allowed to air dry. Gloss was measured as described above. The results are listed in the table below.

| Low Adhesion Coating | | |
| --- | --- | --- |
| Solvent Composition (2-propanol:heptane:xylene) | % Solids | 60° Gloss Reading |
| No LAB | | 89 |
| 51:36:13 | 2.5 | 74.6 |
| 53.7:34:12.3 | 2.36 | 29.2 |
| 56.1:32.3:11.6 | 2.23 | 19.6 |
| 60.3:29.2:20.5 | 2.01 | 16.7 |
| 68.9:23:8.1 | 1.55 | 14.6 |
| 70:22.2:7.8 | 1.5 | 14.3 |

These results indicate the matte effect is dependent on the composition of the solvent and can be controlled by varying solvent ratios. The gloss decreases as the proportion of the poor solvent (2-proponal in this example) increases.

Example 6

Matte-Finish, Low Adhesion Backsize Coating on Polyester Film

A solution of polyvinyloctadecyl carbamate-co-vinyl acetate (5 percent) in heptane/xylene/2-propanol (72:25:3, solution A) was diluted with various amounts of 2-propanol and coated onto unprimed polyester film (3M Company, St. Paul, Minn.) using a No. 14 wire wound rod (RD Specialties, Webster, N.Y.) and allowed to air dry. Gloss was measured using a Micro Tri-Gloss meter (BYK Gardner, Silver Spring, Md.) set to read at 60°. The data is reported in the table below.

| Parts Solution A | Parts 2-propanol | Solution Composition | | | % Solids | 60° Gloss Reading Average |
| --- | --- | --- | --- | --- | --- | --- |
| | | wt % 2-propanol | wt % Heptane | wt % Xylene | | |
| | | No coating | | | | 163.9 |
| 1 | 1 | 52.7 | 35.1 | 12.2 | 2.5 | 144.0 |
| 1 | 2 | 68.8 | 23.2 | 8.1 | 1.67 | 25.2 |
| 1 | 3 | 76.7 | 17.3 | 6 | 1.25 | 12.4 |

These results indicate, in conjunction with the earlier examples, the matte-finish effect is achievable on a variety of substrates.

Example 7

Matte-Finish, Low Adhesion Backsize Coating Using Polyvinyloctadecyl Carbamate-co-Vinyl Acetate Silicone Release Resin Blends A heat curable silicone fluid mixture was prepared by combining 100 parts of a vinylpolydimethylsiloaxane (GE SL6000-D1), 11.3 parts of a vinylpolydimethylsiloaxane/catalyst concentrate (GE SL6010-D1), 0.37 part of an inhibitor (GE SL6040-D1), and 2.34 parts of a dimethyl hydrogen polysiloxane (GE SL6020-D1), all of which are available from GE Silicones, Waterford, N.Y. This mixture was added to solutions of polyvinyloctadecyl carbamate-co-vinyl acetate (2.5 percent) in ethanol/heptane/xylene/2-propanol (50:36:12.5:1.5) to make solutions that contained 1.1 percent, 3.2 percent, and 5.3 percent silicone mixture as a percentage of the solids in the solutions. These solutions were coated onto an "ESTANE" 58309 polyurethane/adhesive laminate prepared as described above using a No.14 wire wound rod (RD Specialties, Webster, N.Y.) and allowed to air dry. The silicone was then cured by heating in an oven at 120° C. for 5 minutes. Gloss and peel adhesion were measured as described above. The results are shown in the table below.

| Wt % Silicones as a percent of total solids | 60° Gloss Reading | Peel Adhesion, grams/inch (N/cm) |
| --- | --- | --- |
| 0% | 11.5 | 293 (1.131) |
| 1.1% | 14.8 | 139 (0.537) |
| 3.2% | 10.1 | 52 (0.201) |
| 5.3% | 15.6 | 56 (0.216) |

These results illustrate a second example of using a polymeric additive to control adhesion/release while maintaining a matte-finish.

Example 8

Matte-Finish, Low Adhesion Backsize Coating Using An Alternative Polyoctadecyl Carbamate-co-Vinyl-Acetate A polyoctadecyl carbamate-co-vinyl acetate made from 88 mole percent hydrolyzed polyvinylacetate commercially available under the trade designation "ESCOAT" P20 (Anderson Chemical Company, Adrian, Miss.) was dried over $CaCl_2$ in a vacuum oven for 24 hours. The dried "ESCOAT" P20 (5.12 grams) was suspended in 44.83 grams toluene and warmed until the polymer dissolved. The solution was cooled to room temperature resulting in a slightly turbid solution. The "ESCOAT" P20/toluene solution was diluted with 2-propanol, as shown in the table below, and coated on an "ESTANE" 58309 polyurethane/adhesive laminate prepared as described above using a No. 3 wire wound rod (RD Specialties, Webster, N.Y.) and allowed to air dry. Gloss was measured. The results are reported in the table below. Gloss decreased as the percent 2-propanol in the solution increased.

Coating of ESCOAT P20 from various SOlvent Mixtures (0.103% solids in ESCOAT/Toluene solution)

| ESCOAT/ Toluene Solution (grams) | 2-propanol (grams) | Solution Composition | | % Solids | 60° Gloss Reading | |
| --- | --- | --- | --- | --- | --- | --- |
| | | wt % IPA | wt % Toluene | | Average | SD |
| 1.00 | 0.00 | 0.00 | 100.00 | 10.25 | 52.7 | 3.4 |
| 2.81 | 1.18 | 31.87 | 68.13 | 7.22 | 47.1 | 2.3 |
| 2.85 | 2.49 | 49.33 | 50.67 | 5.47 | 31.7 | 1.4 |
| 2.44 | 3.03 | 58.05 | 41.95 | 4.57 | 17.8 | 0.4 |
| 1.22 | 2.00 | 64.62 | 35.38 | 3.88 | 17.6* | 0.7 |
| 1.03 | 3.03 | 76.62 | 23.38 | 2.60 | 32.5* | 1.4 |

*These solutions had to be warmed prior to coating to prevent the ESCOAT P20 from precipitating from solution.

These results indicate the matte-finish can be achieved using polyvinyl octadecyl carbamate-co-vinyl acetate made from polyvinyl acetate hydrolyzed from 50 mole percent to 88 mole percent.

Example 9

Effect of LAB Coating on Coefficient of Friction

The LAB solution described in Example 1 was coated onto an "ESTANE" 58309 polyurethane/adhesive laminate and an "ESTANE" 58237 polyurethane/adhesive film laminate (both of which were prepared as described above) using a No. 6 wire wound rod (RD Specialists, Webster, N.Y.) and allowed to air dry. A matte-finish was observed on the coated film. The gloss reading of the uncoated and coated films were 76.5±2.7 and 14.4±2.1 for "ESTANE" 58309 and 50.2±1.4 and 9.2±1.2 for "ESTANE" 58237, respectively. Coefficient of friction was evaluated following ASTM D1894-63 as described above. The coefficient of friction measured for the uncoated and coated films was 0.258±0.017 and 0.242± 0.009 for "ESTANE" 58309 and 0.751±0.025 and 0.223±0.022 for "ESTANE" 58237, respectively.

This example illustrates that for films which have a high coefficient of friction as measured by this test, the coefficient of friction can be reduced by coating with the textured, matte-finish low adhesion backsize coating. As expected, for substrates which already have a low coefficient of friction, the effect of the coating on changing that value is less.

Example 10

Preparation of a Dressing Based on the "ESTANE" 58237 Polyurethane/Adhesive Laminate A dressing was prepared according to the procedure described in Example 1 of U.S. Pat. No. 5,531,855 (Heinecke et al.) to provide a frame delivery system. The "ESTANE" 58237 polyurethane/adhesive laminate was coated with a low adhesion layer to provide the tape-over feature. Using a Gravure station, a 2.2% solids solution (25 parts silicone polyurea and 75 parts polyvinyl N-octadecyl carbamate-co vinylacetate) was coated on the polyurethane (non-adhesive) side of the composite using a 120 lines/inch (47 lines/cm) QCH gravure roll and dried. The solution included: 33 parts polydiorganosiloxane urea-containing component described in Example 1 (consisting of 20 weight percent polydimethylisiloxane and 80 weight percent "DYTEK" EP/IPDI at 5 percent solids in 2-propanol); 100 parts of a solution comprising polyvinyl N-octadecyl carbamate-co-vinylacetate, prepared as described above, 5 percent solids in heptane:xylene:2-propanol (72:25:3 by weight); and 172 parts 2-propanol.

This low adhesion coating/backing/backing (pressure sensitive) adhesive/liner composite web was then slit to proper width to make the size dressing desired. A carrier material (1-80BKG-157 & PE, Daubert Chemical Co.) was then die cut, to form windows which were then removed. The polyethylene side of the carrier material was heat laminated to the backing (over the low adhesion coating) of the above composite. The liner was removed and replaced with a wider liner (2-60BKG-157-99AM, Daubert Chemical Co., Willowbrook, Ill., laminated to the higher release side) sheeted to the proper dressing size using rotary equipment similar to die-cutting/printing machines manufactured by Mark Andy (St. Louis, Mo.). The station modified for heat sealing used roll manufactured by Tokuden Ltd. (Kyoto, Japan).

Example 11

Evaluation of Surface Roughness of LAB Coated Film

To characterize the surface roughness created by coating the LAB from solvent systems that create the matte-finish, the "ESTANE" 58309 polyurethane/adhesive laminate described above was coated with the following low adhesion coatings using a No. 6 wire wound rod (RD Specialists, Webster, N.Y.): A) polyvinyloctadecyl carbamate-co-vinyl acetate having 50 mole percent octadecyl carbamate dissolved in heptane/xylene/2-propanol (73:24:3, 1.6 percent solids); B) polyvinyloctadecyl carbamate-co-vinyl acetate having 50 mole percent octadecyl carbamate dissolved in heptane/xylene/2-propanol (23:8:69, 1.6 percent solids); C) polyvinyloctadecyl carbamate-co-vinyl acetate having 50 mole percent octadecyl carbamate (1.65 percent) and the polydiorganosiloxane urea-containing component described in Example 1 (0.53 percent, 2.2 percent total percent solids) dissolved in heptane/xylene/2-propanol (23:8:69).

A sample of the uncoated laminate (labeled D in the table below) was included in the study. Gloss was measured using the Micro Tri-Gloss meter (BYK Gardner, Silver Springs, Md.) set to read at 60°. Five readings were taken and the average and standard deviation are shown in the table below. Surface roughness was characterized using RST Plus Surface Profiling System as described above.

| | Gloss Readings | | Surface Roughness Characterization | | |
|---|---|---|---|---|---|
| Sample ID | Average | Std. Dev. | $R_q$ | $R_a$ | $R_t$ |
| A | 50.8 | 3.3 | 52 nm | 34 nm | 953 nm |
| B | 7.2 | 0.8 | 193 nm | 141 nm | 3070 nm |
| C | 8.3 | 0.8 | 250 nm | 196 nm | 3060 nm |
| D | 65.8 | 1.1 | 50 nm | 34 nm | 720 nm |

The data shows that the two films coated with the low adhesion coating from solvent systems that generate matte-finish surfaces (Samples B and C) have more surface roughness than the uncoated film. Also, the same low adhesion coating delivered from a solvent system that does not contain sufficient amounts of the poor solvent for the polymer (2-propanol in this case) results in a coating that is essentially equivalent to the uncoated film in both gloss and surface roughness characteristics.

Example 12

Scanning Electron Microscopy Evaluation of LAB Coated Films

Low adhesion backsize coatings on a film surface were further characterized by SEM (scanning electron microscopy) examination to view the surface roughness of film surfaces coated out of a textured, matte-finish generating polymer solvent system and a gloss-finish polymer solvent system. A solution was prepared that contained 3.75 weight percent polyvinyloctadecyl carbamate-co-vinyl acetate and 1.25 weight percent of the polydiorganosiloxane urea-containing component described in Example 1 (5.0% total solids) in 2-propanol/heptane/xylene (27.25:54:18.75). Two low adhesion backsize coating formulations were prepared from this stock solution. A coating composition was prepared by diluting the above described stock solution with 5.1 grams of 2-propanol to make a 2.2% solids solution in 2-propanol/heptane/xylene (68.9:23.1:8). A second coating composition was prepared by diluting this stock solution with 5.1 grams of heptane/xylene (75.5:24.5) to make 2.2% solids solution in 2-propanol/heptane/xylene (11.8:65.9:22.3). The two coating compositions were coated onto "ESTANE" 58309 polyurethane/adhesive laminate as described above using a No. 3 wire wound rod (RD Specialists, Webster, N.Y.). The first solvent system created a textured matte-finish surface, whereas the second solvent system created a glossy surface.

Samples were evaluated for gloss (60° mode) and the gloss was found to be 49.6±1.8 for the glossy sample and 9.4±0.8 for the textured sample. The samples were placed in a LVC-76 low voltage coater (Plasma Sciences, Inc., Lorton, Va.) and sputter coated with approximately 5–7 nm of gold. The samples were then evaluated on a Phillips XL 30 scanning electron microscope (Phillips Electronics, N.V., Roselle, Ill.), using an LAB6 filament.

Representative photomicrographs of the textured sample and the glossy sample are shown in FIG. 5 and FIG. 6, respectively. The SEM photomicrographs demonstrate that polymer deposited from a solvent mixture containing a high percentage of a poor solvent for that polymer mixture resulted in a textured, uniformly distributed matte-finish coating of the LAB. The same polymer, when delivered from a solvent mixture that contains a low percentage of the poor solvent (2-propanol in this case) for the polymer, a smooth, glossy coating of the LAB resulted.

Example 13

Matte-Finish, Low Adhesion Backsize Coating Using Polyvinyl Butyral Resin

To a solution of 4.4 grams of polyoctadecyl carbamate-co-vinyl acetate having 50 mole % octadecyl carbamate (prepared in xylene at 40 percent solids as described above) and 1.58 grams of polyvinyl butyral (available under the trade designation "BUTVAR" B72 from Monsanto Company, St. Louis, Mo.) in a solvent mixture of 178.6 grams of 2-propanol, 20.6 grams of xylene and 59.9 grams of heptane was added 0.40 grams of 5,000 Mn polydimethylsiloxane diamine (PDMS, prepared following U.S. Pat. No. 5,512,650) and 0.50 grams of 1,3-diaminopentane (available under the trade designation "DYTEK" EP from DuPont) with stirring at 25° C. Next, 1.10 grams of isophorone diisocyanate (IPDI available from Huls or Bayer) was added at 25° C. with stirring and a slow nitrogen purge. The mixture was stirred for 30 minutes, and, in the presence of the polyoctadecyl carbamate-co-vinyl acetate and the polyvinyl butyral, the IPDI reacted with the PDMS diamine and the 1,3-diaminopentane to form a polydiorganosiloxane urea-containing component with 20 weight % PDMS and 80 weight % 1,3-diaminopentane/IPDI. The final product mixture was a homogeneous, hazy, approximately 3% solids solution of a polymer component (polyoctadecyl carbamate-co-vinyl acetate), a polydiorganosiloxane urea-containing component and polyvinyl butyral in a 55:25:20 solids weight ratio.

A similar solution was prepared but without the added polyvinyl butyral. This resulted in a homogeneous, hazy approximately 2.4% solids, solution of a polymer component (polyoctadecyl carbamate-co-vinyl acetate) and a polydiorganosiloxane urea-containing component in a 68.8:31.2 weight ratio.

The two solutions were coated onto a "ESTANE" 58309 polyurethane/adhesive laminate and "ESTANE" 58237 polyurethane/adhesive laminate as described above using a #9 wire wound rod (RD Specialists, Webster, N.Y.) and allowed to air dry. A matte-finish was observed on the coated films.

To measure durability, samples of the coated films were abraded using a BYK-Gardner Abrasion Tester (model AG-8100, BYK-Gardner, Silver Spring, Md.). The sandpaper attachment (AG8117, KYK-Gardner, Silver Spring, Md.) was used which was fitted with a piece of twill-jean fabric (PN 71750 from Electron Microscope Sciences, Fort Washington, Pa.). The sled was drawn back and forth for 200 cycles and the gloss measured before abrasion and after 50, 100 and 200 abrasion cycles. The table below shows the Δ gloss (gloss after abrasion-gloss before abrasion) of the matte LAB coatings with and without the added polyvinyl butyral on the polyurethane/adhesive laminates.

| Laminate | Additive | 50 cyles (60° Δ Gloss) | | 100 cycles (60° Δ Gloss) | | 200 cycles (60° Δ Gloss) | |
|---|---|---|---|---|---|---|---|
| | | Ave. | st. dev. | ave. | st. dev. | ave. | st. dev. |
| ESTANE 58237 | None | 15.8 | 3.3 | 18.5 | 2.7 | 21.0 | 2.7 |
| ESTANE 58237 | BUTVAR B72 | 3.8 | 0.8 | 6.9 | 2.6 | 12.4 | 4.1 |
| ESTANE 58309 | None | 12.3 | 1.1 | 15.5 | 1.1 | 30.6 | 2.2 |
| ESTANE 58309 | BUTVAR B72 | 3.9 | 0.8 | 8.8 | 0.5 | 14.4 | 4.2 |

Example 14

Matte-Finish, Low Adhesion Backsize Coating Using Polyethyloxazoline

To a solution of 2.5 grams polyoctadecyl carbamate-co-vinyl acetate having 50 mole % octadecyl carbamate (prepared in xylene at 40 percent solids as described above), in 47.5 grams of a solvent blend of heptane/xylene/2-propanol (72/25/3 weight ratio) was added 102.5 grams 2-propanol. This solution was divided into 10 gram samples and to these samples was added 0 gram, 0.107 gram, 0.204 gram, 0.304 gram, 0.435 gram, and 0.554 gram polyethyloxazoline (PeOX 50; Dow Chemical Co., Midland, Miss.). In addition, polyethyloxazoline was dissolved in 2-propanol to make a 5% solids solution. These solutions were coated onto Estane 58309 (B F Goodrich, Cleveland, Ohio) using a 9# wire wound rod (RD Specialities, Webster, N.Y.) and allowed to air dry. A matte finish was observed on the coated film. Gloss was measured using a Micro Tri-Gloss meter (BYK Gardner, Silver Spring, Md.) set to read at 60 degrees. Gloss is reported in the table below:

| Wt. % Polyethyloxazoline in LAB coating | Gloss Readings | |
|---|---|---|
| | Average | Std. Dev. |
| 0 | 14.3 | 0.2 |
| 33 | 10.5 | 0.4 |
| 48 | 11.0 | 0.4 |
| 58 | 15.9 | 1.6 |
| 66 | 18.9 | 0.2 |
| 72 | 25 | 2.1 |
| 100 | 57.4 | 3.0 |

The results show significant amounts of polyethyloxazoline can be added and still obtain a matte finish.

These samples were evaluated for durability by rubbing the thumb of the hand several times over the film. The sample with no polyethyloxazoline lost the matte finish after several rubs. The samples with added polyethyloxazoline were significantly more durable and could not easily be removed by rubbing.

The complete disclosure of all patents, patent documents, and publications cited herein are incorporated be reference. The foregoing detailed description and examples have been given for clarity of understanding only. No unnecessary limitations are to be understood therefrom. The invention is not limited to the exact details shown and described, for variations obvious to one skilled in the art will be included within the invention defined by the claims.

What is claimed is:

1. An article comprising:
   a) a substrate; and
   b) a textured, matte-finish, low adhesion backsize coating on one surface of the substrate, wherein the coating comprises a phase-separated polyvinyl carbamate having nitrogen-bonded hydrocarbon side chains which provide terminal alkyl groups more than five carbons in length.

2. The article of claim 1 wherein the backsize coating has a 60° gloss reading of no greater than about 40.

3. The article of claim 2 wherein the backsize coating has a 60° gloss reading of no greater than about 30.

4. The article of claim 3 wherein the backsize coating has a 60° gloss reading of about 5 to about 15.

5. The article of claim 1 wherein the backsize coating has a coefficient of friction that is less than that of the uncoated substrate.

6. The article of claim 5 wherein the substrate comprises polyurethane and the coefficient of friction of the backsize coating is no greater than about 0.4.

7. The article of claim 1 wherein the backsize coating has a surface roughness that is greater than that of the uncoated substrate.

8. The article of claim 1 wherein the polyvinyl carbamate comprises at least about 50 mole percent nitrogen-bonded hydrocarbon side chains.

9. The article of claim 1 wherein the alkyl groups are at least 14 carbons in length.

10. The article of claim 1 further comprising a pressure sensitive adhesive coated on an opposite surface of the substrate.

11. The article of claim 1 wherein the coating further comprises a release modifying material.

12. The article of claim 11 wherein the release modifying material is formed in the presence of the polyvinyl carbamate.

13. The article of claim 11 wherein the release modifying material is selected from the group of an organopolysiloxane urea, an organopolysiloxane diamine, a silicone resin, a silicone acrylate, and a fluoropolymer.

14. The article of claim 1 which is a wound dressing.

15. The article of claim 1 which is a target strip.

16. The article of claim 1 wherein the coating further comprises a durability enhancing polymer.

17. The article of claim 16 wherein the durability enhancing polymer is selected from the group of polyvinyl butyral, polyethyloxazoline, and combinations thereof.

18. An article comprising:
   a) a substrate; and
   b) a textured, matte-finish, low adhesion backsize coating on one surface of the substrate, wherein the coating is formed from a composition comprising polyvinyl carbamate having nitrogen-bonded hydrocarbon side chains which provide terminal alkyl groups more than five carbons in length; wherein the gloss of the backsize coating is less than that of the uncoated substrate and less than that of the substrate coated with the same coating composition that is not textured; and further wherein the coating is formed from a composition comprising a solvent system comprising at least one good solvent for the polyvinyl carbamate and at least one poor solvent for the polyvinyl carbamate in a ratio sufficient to cause precipitation of the polymer upon evaporation of the solvent system.

19. The article of claim 18 wherein the backsize coating has a 60° gloss reading of no greater than about 40.

20. The article of claim 19 wherein the backsize coating has a coefficient of friction less than that of the uncoated substrate.

21. The article of claim 20 wherein the backsize coating has a surface roughness greater than that of the uncoated substrate.

22. The article of claim 18 further comprising a pressure sensitive adhesive coated on an opposite surface of the substrate.

23. The article of claim 18 wherein the backsize coating is formed from a composition further comprising a release modifying material.

24. The article of claim 23 wherein the release modifying material is selected from the group of an organopolysiloxane urea, an organopolysiloxane diamine, a silicone resin, a silicone acrylate, and a fluoropolymer.

25. The article of claim 18 which is a wound dressing.

26. The article of claim 18 which is a target strip on an object.

27. The article of claim 18 wherein the coating further comprises a durability enhancing polymer.

28. The article of claim 27 wherein the durability enhancing polymer is selected from the group of polyvinyl butyral, polyethyloxazoline, and combinations thereof.

29. A method of preparing an article comprising a substrate on which is coated a textured, matte-finish, low adhesion backsize coating on one surface of the substrate, the method comprising coating a composition comprising polyvinyl carbamate having nitrogen-bonded hydrocarbon side chains which provide terminal alkyl groups more than five carbons in length and a solvent system comprising at least one good solvent for the polyvinyl carbamate and at least one poor solvent for the polyvinyl carbamate in a ratio sufficient to cause precipitation of the polymer upon evaporation of the solvent system.

30. The method of claim 29 wherein the good solvent is an aromatic solvent, an alkane, or mixtures thereof.

31. The method of claim 29 wherein the poor solvent is an alcohol.

32. The method of claim 29 wherein the solvent system comprises an aromatic solvent, an alkane, and a lower alcohol.

33. The method of claim 32 wherein the solvent system comprises xylene, heptane, and 2-propanol.

34. The method of claim 33 wherein the 2-propanol is present in an amount of at least about 50 weight percent, based on the total weight of the solvent system.

35. The method of claim 29 wherein the composition further comprises a release modifying material.

36. The method of claim 35 wherein the release modifying material is selected from the group of an organopolysiloxane urea, an organopolysiloxane diamine, a silicone resin, a silicone acrylate, and a fluoropolymer.

37. The method of claim 36 wherein the release modifying material is formed in the presence of the polyvinyl carbamate.

38. The method of claim 29 wherein the coating further comprises a durability enhancing polymer.

39. The method of claim 38 wherein durability enhancing the polymer is selected from the group of polyvinyl butyral, polyethyloxazoline, and combinations thereof.

40. The method of claim 29 wherein the gloss and coefficient of friction of the backsize coating is less than that of the uncoated substrate and less than that of the substrate coated with the same coating composition that is not textured.

41. The method of claim 40 wherein the backsize coating has a 60° gloss reading of no greater than about 40.

42. A method of preparing an article comprising a substrate on which is coated a textured, matte-finish, low adhesion backsize coating on one surface of the substrate, the method comprising coating a composition comprising a low adhesion backsize polymer and a solvent system comprising a mixture of solvents in a ratio sufficient to cause precipitation of the polymer upon evaporation of the solvent system.

43. An article comprising:
a) a substrate; and
b) a non-particle loaded, non-embossed, and non-mechanically roughened, textured, matte-finish, low adhesion backsize coating on one surface of the substrate, wherein the coating comprises polyvinyl carbamate having nitrogen-bonded hydrocarbon side chains which provide terminal alkyl groups more than five carbons in length.

* * * * *